United States Patent [19]

Muryobayashi et al.

[11] 4,443,478
[45] Apr. 17, 1984

[54] PROSTAGLANDIN ANALOGUES

[75] Inventors: Takashi Muryobayashi; Hajimu Miyake; Takashi Yamato, all of Takatsuki, Japan

[73] Assignee: Ono Pharmaceutical Co., Ltd., Osaka, Japan

[21] Appl. No.: 392,676

[22] Filed: Jun. 28, 1982

[30] Foreign Application Priority Data

Jun. 29, 1981 [JP] Japan .................. 56-99724
May 25, 1982 [JP] Japan .................. 57-87229

[51] Int. Cl.³ .................. C07C 177/00; A61K 31/215
[52] U.S. Cl. .................. 424/331; 568/330; 568/379; 536/103; 549/465
[58] Field of Search .............. 568/379, 330; 424/331; 536/103

[56] References Cited

U.S. PATENT DOCUMENTS

| | | | | |
|---|---|---|---|---|
| 4,170,597 | 10/1979 | Wissner | ............ | 560/121 |
| 4,172,839 | 10/1979 | Wissner | ............ | 560/121 |
| 4,197,245 | 4/1980 | Wissner | ............ | 560/121 |
| 4,202,822 | 5/1980 | Wissner | ............ | 560/121 |
| 4,205,178 | 5/1980 | Axen | ............ | 560/121 |
| 4,212,969 | 7/1980 | Wissner | ............ | 560/121 |
| 4,215,142 | 7/1980 | Hayashi | ............ | 424/305 |
| 4,235,797 | 11/1980 | Wissner | ............ | 560/121 |
| 4,254,036 | 3/1981 | Wissner | ............ | 260/340.9 P |
| 4,254,285 | 3/1981 | Wissner | ............ | 560/121 |

*Primary Examiner*—Robert Gerstl
*Attorney, Agent, or Firm*—Stevens, Davis, Miller & Mosher

[57] ABSTRACT

Prostaglandin $E_1$ analogues of general formula:

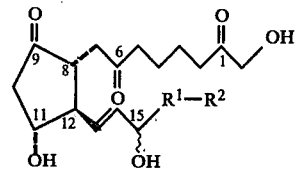

[wherein $R^1$ represents a bond or a straight- or branched-chain alkylene group containing from 1 to 5 carbon atom(s), and $R^2$ represents a hydrogen atom, a straight- or branched-chain alkyl group containing from 1 to 8 carbon atom(s), a cycloalkyl group containing from 4 to 7 carbon atoms in the ring and unsubstituted or substituted by at least one stright- or branched-chain alkyl group containing from 1 to 8 carbon atom(s) or a phenyl or phenoxy group unsubstituted or substituted by at least one halogen atoms, trifluoromethyl group or straight- or branched-chain alkyl group containing from 1 to 4 carbon atom(s), with the proviso that, when $R^1$ represents a bond, $R^2$ does not represent a phenoxy group,] possess inhibitory activity or gastric ulceration and cytoprotective activity.

10 Claims, No Drawings

PROSTAGLANDIN ANALOGUES

DESCRIPTION

This invention is concerned with new prostaglandin analogues.

Prostaglandins are derivatives of prostanoic acid which has the following formula:

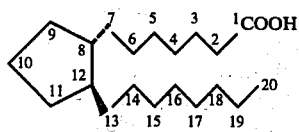

Various types of prostaglandins are known, the types depending inter alia on the structure and substituents on the alicyclic ring. For example, the alicyclic ring of prostaglandin E(PGE) has the structure:

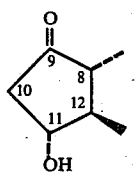

The dotted lines in the foregoing formulae and in other formulae throughout this specification denote, in accordance with generally accepted rules of nomenclature, that the attached grouping lies behind the general plane of the ring system, i.e. that the grouping is in α-configuration, and the thickened lines denote that the grouping lies in front of the general plane of the system, i.e. that the grouping is in β-configuration. The wavy line in other formulae throughout this specification indicates that the grouping is in α- or β-configuration.

Such compounds are sub-classified according to the position of double bond(s) in the side chain(s) attached to the 8- and 12-positions of the alicyclic ring. Thus PG$_1$ compounds have a trans-double bond between C$_{13}$–C$_{14}$(trans-$\Delta^{13}$) and PG$_2$ compounds have a cis-double bond between C$_5$–C$_6$ and a trans-double bond between C$_{13}$–C$_{14}$ (cis-$\Delta^5$, trans-$\Delta^{13}$). For example, prostaglandin E$_1$ (PGE$_1$) is characterised by the following structure (III):

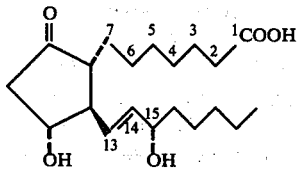

The structure of PGE$_2$, as a member of the PG$_2$ group, corresponds to that of formula (III) with a cis-double bond between the carbon atoms in positions 5 and 6. Compounds in which the double bond between the carbon atoms in positions 13 and 14 of members of the PG$_1$ group is replaced by ethylene are known as dihydroprostaglandins, e.g. dihydro-prostaglandin-E$_1$ (dihydro-PGE$_1$).

Moreover, when one or more methylene groups are eliminated from the aliphatic group attached to the 12-position of the alicyclic ring of the prostaglandins the compounds are known, in accordance with the usual rules of organic nomenclature, as nor-prostaglandins and, when more than one methylene group is eliminated, the number is indicated by di- tri- etc. before the prefix "nor".

Prostaglandins are generally known to possess pharmacological properties, for example they stimulate smooth muscle, have hypotensive, diuretic, bronchodilating and antilipolytic activites, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. PGE$_1$ inhibits blood platelet aggregation and also removes the thrombus and prevents thrombosis. PGE's have a stimulating effect on smooth muscle and increase the intestinal peristalsis; these actions indicate therapeutic utility on post-operative ileus and as purgatives. PGE's may also be used as oxytocics, as abortifacients in the first and second trimesters; in the post-labour abortion of the placenta, and as oral contraceptives because they regulate the sexual cycle of female mammals. PGE's have vasodilator and diuretic activities. They are useful for improvement in patients suffering from cerebral vascular disease because they increase the cerebral blood flow, and are also useful in the treatment of asthmatic conditions in patients because of their bronchodilating activity.

Recently, it has been found that a kind of prostaglandin has a cytoprotective activity and is useful in the treatment of cyto-damage in liver diseases and pancreatic diseases [cf. Gastronenterology, 78, 777–781 (1980) and ibid, 81, 211–217 (1981), and Folia Histochemica et Cytochemica, 18, 311–318 (1980)].

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found, after research and experimentation, that by replacing the hydrogen atoms attached to the C-6 carbon atom by an oxo group (i.e. =O) and further by replacing the carboxy group attached to the C-2 carbon atom of prostaglandin E$_1$ and certain analogues thereof by a glycoloyl group (i.e.—CO—CH$_2$—OH), new prostaglandin E$_1$ analogues are obtained which possess strong inhibitory activity on gastric ulceration and strong cytoprotective activity.

The present invention accordingly provides the new prostaglandin E$_1$ analogues of the general formula:

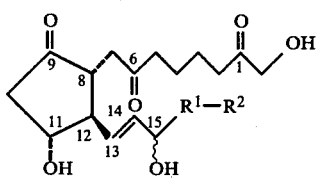

[wherein R¹ represents a direct bond or a straight- or branched-chain alkylene group containing from 1 to 5 carbon atom(s), and R² represents a hydrogen atom, a straight- or branched-chain alkyl group containing from 1 to 8 carbon atom(s), a cycloalkyl group containing from 4 to 7 carbon atoms in the ring and unsubstituted or substituted by at least one straight- or branched-chain alkyl group containing from 1 to 8 carbon atom(s) or a phenyl or phenoxy group unsubstituted or substituted by at least one halogen atom, trifluoromethyl group or straight- or branched-chain alkyl group containing from 1 to 4 carbon atom(s), with the proviso that, when R¹ represents a direct bond, R² does not represent a phenoxy group] and cyclodextrin clathrates thereof. Preferably the hydroxy group attached to the C-15 carbon atom of formula (IV) is in α-configuration.

The present invention is concerned with all compounds of general formula (IV) in the 'natural' form or its enantiomeric form, or mixtures thereof, more particularly the racemic form consisting of equimolecular mixtures of natural and its enantiomeric form.

As will be apparent to those skilled in the art, the compounds depicted in general formula (IV) have at least four centres of chirality, these four centres of chirality being at the C-8, C-11, C-12 and C-15 carbon atoms. Still further centres of chirality may occur when R² is a branched-chain alkyl group or an alkyl-substituted cycloalkyl group or R¹ is a branched-chain alkylene group. The presence of chirality leads, as is well known, to the existence of isomerism. However, the compounds of general formula (IV) all have such a configuration that the side-chains attached to the ring carbon atoms in the positions identified as 8 and 12 are trans with respect to each other. Accordingly, all isomers of general formula (IV), and mixtures thereof, which have those side-chains attached to the ring carbon atoms in positions 8 and 12 are in the trans configuration and have hydroxy groups as depicted in the 11- and 15-positions are to be considered within the scope of formula (IV).

Examples of the straight- or branched-chain alkylene group containing from 1 to 5 carbon atom(s) represented by R¹ are methylene, ethylene, propylene, butylene and pentylene and their isomers.

Examples of the straight- or branched-chain alkyl group containing from 1 to 8 carbon atom(s) represented by R² are methyl, ethyl, propyl, butyl, pentyl, hexyl, heptyl and octyl and their isomers.

Examples of the cycloalkyl group containing from 4 to 7 carbon atoms unsubstituted or substituted by at least one alkyl group containing from 1 to 8 carbon atom(s) represented by R² are cyclobutyl,1-propylcyclobutyl, 1-butylcyclobutyl, 1-pentylcyclobutyl, 1-hexylcyclobutyl, 2-methylcyclobutyl, 2-propylcyclobutyl, 3-ethylcyclobutyl, 3-propylcyclobutyl, 2,3,4-triethylcyclobutyl, cyclopentyl, 1-methylcyclopentyl, 3-methylcyclopentyl, 2,2-dimethylcyclopentyl, 3-ethylcyclopentyl, 3-propylcyclopentyl, 3-butylcyclopentyl, 3-tert-butylcyclopentyl, 1-methyl-3-propylcyclopentyl, 2-methyl-3-propylcyclopentyl, 2-methyl-4-propylcyclopentyl, 2-pentylcyclopentyl, cyclohexyl, 1-methylcyclohexyl, 3-ethylcyclohexyl, 3-isopropylcyclohexyl, 4-methylcyclohexyl, 4-ethylcyclohexyl, 4-propylcyclohexyl, 4-butylcyclohexyl, 4-tert-butylcyclohexyl, 2,2-dimethylcyclohexyl, 2,6-dimethylcyclohexyl, 2,6-dimethyl-4-propylcyclohexyl and cycloheptyl.

Preferably the grouping —R¹—R² represents pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, hexyl, 1-methylhexyl, 2-methylhexyl, 1,1-dimethylhexyl, 1-ethylhexyl, 2-ethylhexyl, heptyl, 2-methylheptyl, 2-ethylheptyl, nonyl, undecyl, cyclobutyl, 1-propylcyclobutyl, 1-butylcyclobutyl, 1-pentylcyclobutyl, 1-hexylcyclobutyl, 2-methylcyclobutyl, 2-propylcyclobutyl, 3-ethylcyclobutyl, 3-propylcyclobutyl, 2,3,4-triethylcyclobutyl, cyclopentyl, cyclopentylmethyl, 2-cyclopentylethyl, 1-cyclopentylethyl, 3-cyclopentylpropyl, 2-cyclopentylpropyl, 2-pentylcyclopentyl, 2,2-dimethylcyclopentyl, 3-methylcyclopentyl, 3-ethylcyclopentyl, 3-propylcyclopentyl, 3-butylcyclopentyl, 3-tert-butylcyclopentyl, 1-methyl-3-propylcyclopentyl, 2-methyl-3-propylcyclopentyl, 2-methyl-4-propylcyclopentyl, cyclohexyl, cyclohexylmethyl, 2-cyclohexylethyl, 1-cyclohexylethyl, 3-cyclohexylpropyl, 1-methyl-2-cyclohexylethyl, 2-cyclohexylpropyl, 1-methyl-1-cyclohexylethyl, 4-cyclohexylbutyl, 3-ethylcyclohexyl, 3-isopropylcyclohexyl, 4-methylcyclohexyl, 4-ethylcyclohexyl, 4-propylcyclohexyl, 4-butylcyclohexyl, 4-tertbutylcyclohexyl, 2,6-dimethylcyclohexyl, 2,2-dimethylcyclohexyl, 2,6-dimethyl-4-propylcyclohexyl, 1-methylcyclohexylmethyl, cycloheptyl, cycloheptylmethyl, 2-cycloheptylethyl, 1-cycloheptylethyl, phenyl, benzyl, 1-phenylethyl, 2-phenylethyl, (3-chlorophenoxy)methyl, (4-chlorophenoxy) methyl, (3-trifluoromethylphenoxy)methyl or phenoxymethyl.

Preferably R¹ represents a direct bond or a methylene group. Preferably R² represents an n-pentyl, n-hexyl or n-heptyl group unsubstituted or substituted by one or more (preferably one or two) methyl group(s), or represents a cyclopentyl or cyclohexyl group, unsubstituted or substituted by an alkyl group containing from 1 to 8 carbon atom(s), or a phenoxy group unsubstituted or substituted by a chlorine atom.

Particularly preferred prostaglandin analogues of general formula (IV) are (i) compounds wherein R¹ represents a bond, and R² represents a cycloalkyl group containing from 4 to 7 carbon atoms in the ring (preferably cyclopentyl) and unsubstituted or substituted by a straight- or branched-chain alkyl group containing from 1 to 8 (preferably 1 to 4) carbon atom(s), and (ii) compounds wherein the grouping —R¹—R² represents an n-pentyl, n-hexyl or n-heptyl group unsubstituted or substituted by one or more (preferably one or two) methyl group(s).

According to a feature of the present invention, the prostaglandin E₁ analogues of general formula (IV) may be prepared by the hydrolysis to hydroxy groups of the groups OR³ and the 3-oxapentan-2-yloxy group of a compound of general formula:

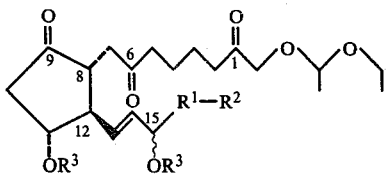

(V)

[wherein $R^3$ represents a tetrahydrofuran-2-yl group or a tetrahydropyran-2-yl group, each such group being unsubstituted or substituted by at least one alkyl group, or represents a 1-ethyoxyethyl group, and the other symbols are as hereinafter defined].

The groups $OR^3$ and the 3-oxapentan-2-yloxy group of the compounds of general formula (V) may be converted to hydroxy groups by mild acidic hydrolysis (1) with an aqueous solution of an organic acid such as acetic acid, propionic acid, oxalic acid or p-toluenesulphonic acid, or an aqueous solution of an inorganic acid, such as hydrochloric acid or sulphuric acid, advantageously in the presence of an inert organic solvent miscible with water, e.g. a lower alkanol such as methanol or ethanol (preferably methanol), or an ether such as 1,2-dimethoxyethane, dioxan or tetrahydrofuran (preferably tetrahydrofuran), at a temperature ranging from ambient to 75° C. (preferably at a temperature below 45° C.), or (2) with an anhydrous solution of an organic acid such as p-toluenesulphonic acid or trifluoroacetic acid in a lower alkanol such as methanol or ethanol at a temperature ranging from 10° to 45° C. Advantageously the mild hydrolysis may be carried out with a mixture of hydrochloric acid, water and tetrahydrofuran, a mixture of hydrochloric acid, water and methanol, a mixture of acetic acid, water and tetrahydrofuran, or a mixture of p-toluenesulphonic acid and methanol.

Compounds of general formula (V) may be prepared by the oxidation of a compound of the general formula:

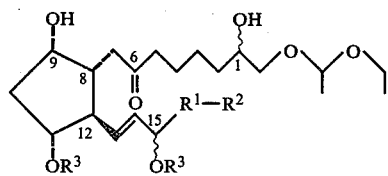

(VIa)

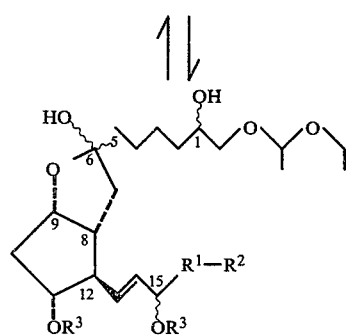

(VIb)

[wherein the various symbols are a hereinbefore defined, and the arrows ↑ ↓ indicate that the compounds are in equilibrium] by methods known per se for the conversion of hydroxy groups in the 1- and 9-position of a prostaglandin compound to oxo groups. By the expression "methods known per se" as used in this specification is meant methods heretofore used or described in the chemical literature.

Preferably the oxidation is carried out under mild, neutral conditions, for example, by reaction with (1) dimethyl sulphide-N-chlorosuccinimide complex, thionanisole-N-chlorosuccinimide complex, dimethyl sulphide-chlorine complex or thioanisole-chlorine complex in a haloalkane, e.g. chloroform, methylene chloride or carbon tetrachloride, or toluene at a temperature of from −30° C. to 0° C. [cf. J.Am. Chem. Soc. 94, 7586 (1972)], (2) chromium trioxide-pyridine complex, e.g. Collins' reagent, in a haloalkane, e.g. chloroform, methylene chloride or carbon tetrachloride, at a temperature of from 0° C. to ambient, preferably at 0° C., or (3) Jones' reagent in the presence of acetone and dilute sulphuric acid at a temperature of from 0° C. to ambient.

Compounds of general formula (VI) [(VIa) and (VIb)] may be prepared by dehydrohalogenation and further hydrolysis of compounds of general formula:

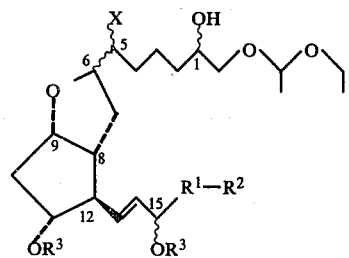

(VII)

[wherein X represents a bromine or iodine atom, and the other symbols are as hereinbefore defined].

The dehydrohalogenation may be carried out with a known dehydrohalogenation reagent, for example (1) when X represents a bromine atom, a bicycloamine such as DBU (i.e. 1,5-diazabicyclo[5.4.0]undecene-5), DBN (i.e. 1,5-diazabicyclo[4.3.0]nonene-5) or DABCO (i.e. 1,4-diazabicyclo[2.2.2]octane), or an alkali metal, e.g. sodium or potassium, alcoholate containing from 1 to 4 carbon atoms, or (2) when X represents an iodine atom, a bicycloamine such as DBN, DBU or DABCO, or an alkali metal, e.g. sodium or potassium, alcoholate containing from 1 to 4 carbon atoms, superoxide, carbonate, hydroxide, benzoate, acetate, trifluoroacetate or bicarbonate, or silver acetate, or tetramethylammonium superoxide. The reaction may be carried out at a temperature from ambient to 110°, preferably at a temperature from ambient to 80° C., and (1) when the reagent is a bicycloamine, optionally in the presence of an inert organic solvent, preferably in the absence of an inert organic solvent or in the presence of toluene or benzene, or (2) when the reagent is other than a bicycloamine, in the presence of an inert organic solvent, e.g. an alkanol containing from 1 to 4 carbon atoms, such a methanol or ethanol, or N,N-dimethylformamide.

The further hydrolysis must be carried out carefully to avoid the elimination of the groups $R^3$, and may be carried out with an aqueous solution of an organic acid, e.g. acetic acid, propionic acid, oxalic acid or p-toluenesulphonic acid, or an aqueous solution of an inorganic acid, e.g. hydrochloric or sulphuric acid, in the presence or absence of an inert organic solvent miscible with water, e.g. an ether such as 1,2-dimethoxyethane, dioxan or tetrahydrofuran (preferably tetrahydrofuran), at a temperature of from 0° C. to 75° C. (preferably from 0° C. to ambient). Advantageously the hydrolysis may be carried out with a mixture of acetic acid, water and tetrahydrofuran, a mixture of dilute hydrochloric acid and tetrahydrofuran, or dilute hydrochloric acid. The progress of the hydrolysis is preferably monitored by thin layer chromatography to avoid elimination of the groups $R^3$.

Compounds of general formula (VII) may be prepared by reacting a compound of general formula:

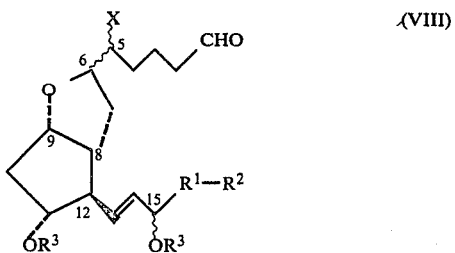

[wherein the various symbols are as hereinbefore defined] with a compound of the formula:

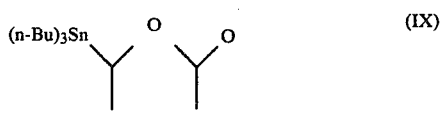

The reaction may be carried out by methods known per se, for example in an inert organic solvent, e.g. an ether such as diethyl ether, tetrahydrofuran or 1,2-dimethoxyethane, or a hydrocarbon such as n-hexane or n-heptane, or mixture thereof, at a temperature of from 0° C. to −80° C. by dropwise addition of n-butyl lithium and (2,4-dioxa-3-methylhexyl)-tri-n-butyl stannane, preferably in tetrahydrofuran at −78° C. by dropwise addition of n-butyl lithium in hexane into (2,4-dioxa-3-methylhexyl)-tri-n-butyl stannane and further by dropwise addition of an aldehyde compound of general formula (VIII) in tetrahydrofuran into the above obtained solution [cf. J. Am. Chem. Soc., 100, 1481 (1978)].

Compounds of general formula (VIII) may be prepared by reducing the alkoxycarbonyl group of a compound of general formula:

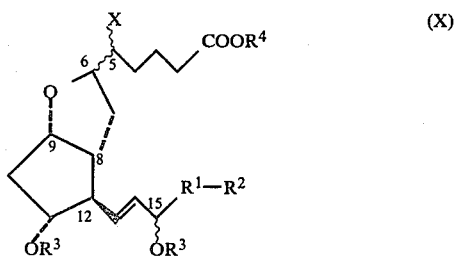

[wherein $R^4$ represents a straight- or branched-chain alkyl group containing from 1 to 4 carbon atom(s), and the other symbols are as hereinbefore defined] to a formyl group.

The reduction may be carried out, for example, in an inert organic solvent e.g. hexane, tetrahydrofuran or toluene, using a reducing agent e.g. diisobutyl aluminium hydride (DIBAL), at a temperature of from 0° C. to −80° C.; the reduction is preferably effected in toluene at −78° C. by dropwise addition of diisobutyl aluminium hydride.

The compounds of general formula (X) are known or may be prepared by methods known per se [see our U.S. Pat. No. 4,215,142, our French Patent Publication No. 2403333, our British Patent Publication No. 2,006,753 and our German Patent Publication No. 2840032.].

The compounds of general formula (IX) are also known compounds [see J. Am. Chem. Soc., 100, 1481, (1978)].

Cyclodextrin clathrates of the prostaglandin analogues of general formula (IV) may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. α-, β- or γ-Cyclodextrins or mixtures thereof may be used in the preparation of the cyclodextrin clathrates. Conversion into their cyclodextrin clathrates serves to increase the stability of the prostaglandin analogues.

The prostaglandin $E_1$ analogues of general formula (IV) and their cyclodextrin clathrates show, in particular, inhibitory activity on gastric acid secretion and gastric ulceration in a selective fashion among the various pharmacological activities which are typical of prostaglandins, and strong cytoprotective activity, and are useful in the prevention and treatment of gastric ulceration, and diseases of various organisms or systems in human beings induced by cyto-damage, for example, liver diseases such as hepatitis, pancreatic diseases such as pancreatitis, and diabetes mellitus and its complications. In addition to the abovementioned valuable pharmacological property the compounds of general formula (IV) and their cyclodextrin clathrates possess relatively weak other prostaglandin-like activities such as hypotensive activity, inhibitory activity on blood platelet aggregation and uterine contractile activity.

For example, in standard laboratory tests, (i) in stress ulceration of rats [produced according to the methods of Takagi and Okabe, Jap. J. Pharmac., 18, 9–18 (1968) by soaking rats in a water bath at 19° C. for 6 hours], 1-hydroxymethyl-11α,15(S)-dihydroxy-17(S),20-dimethylprosttrans-13-ene-1,6,9-trione produced 56.8% and 91.8% inhibition of stress ulceration by oral administration at the doses of 20 and 50 μg/kg animal body weight, respectively, (ii) in carbon tetrachloride-induced liver damage in rats, 1-hydroxymethyl-11α,15(S)-dihydroxy-17(S),20-dimethylprosttrans-13-ene-1,6,9-trione produced 58.0% and 59.7% inhibition of plasma GOT (glutamic oxalacetic transaminase) and GPT (glutamic pyruvic transaminase) by oral administration at the dose of 50 μg/kg animal body weight in comparison with controls and produced 61.4% and 48.7% inhibition of plasma GOT and GPT by subcutaneous administration at the dose of 20 μg/kg animal body weight in comparison with controls; 1-hydroxymethyl-11α,15(S)-dihydroxy-15-(3-butylcyclopentyl)-16,17,18,19,20-pentanorprost-trans-13-ene-1,6,9-trione produced 54.9% and 48.6% inhibition of plasma GOT and GPT by oral administration at the dose of 50 μg/kg animal body weight in comparison with controls; and 1-hydroxymethyl-11α,15(S)-dihydroxy-15-(3-propylcyclopentyl)-16,17,18,19,20-pentanorprost-trans-13-ene-1,6,9-trione produced 46.7% and 45.1% inhibition of plasma GOT and GPT by oral administration at the dose of 50 μg/kg animal body weight in comparison with controls, (iii) in α-naphthylisothiocyanate-induced liver damage in rats, 1-hydroxymethyl-11α,15(S)-dihydroxy-17(S),20-dimethylprost-trans-13-ene-1,6,9-trione produced 49.0%, 53.7% and 21.2% inhibition of plasma GOT, GPT and bilirubin by oral administration at the dose of 100 μg/kg animal body weight in comparison with controls, respectively; 1-hydroxymethyl-11α,15(S)-dihydroxy-15-(3-propylcyclobutyl)-16,17,18,19,20-pentanorprost-trans-13-ene-1,6,9-trione produced 53.1%, 61.3% and 30.3% inhibition of plasma GOT, GPT and bilirubin by oral administration at the dose of 100 μg/kg animal body weight in comparison with controls, respectively; 1-hydroxymethyl-11α,15(S)-dihydroxyl-15-(3-butylcyclopentyl)-16,17,18,19,20-pentanorprost-trans-13-ene-1,6,9-trione produced 30.3%, 41.7% and 15.2% inhibition of plasma GOT, GPT and bilirubin by oral administration at the dose of 100 μg/kg animal body weight in comparison with control, respectively, (iv) in D(+)-galactoseamine-induced liver damage in rats; 1-hydroxymethyl-11α,15(S)-dihydroxy-15-(3-butylcyclopentyl)-16,17,18,19,20-pentanorprost-trans-13-ene-1,6,9-trione produced 57.0%, 54.0% and 63.0% inhibitions of plasma GOT, GPT and bilirubin by oral administration at the dose of 100 μg/kg animal body weight in comparison with control, respectively;

(v) by intravenous administration to the allobarbitalanaesthetized dog, 1-hydroxymethyl-11α,15(S)-dihydroxy-17(S), 20-dimethylprost-trans-13-ene,1,6,9-trione produced a fall in blood pressure of 6 mm Hg and 15 mm Hg lasting 14 and 29 minutes at the doses of 0.3 and 0.5 μg/kg animal body weight, respectively; 1-hydroxymethyl-11α,15(S)-dihydroxy-15-(3-butylcyclopentyl)-16,17,18,19,20-pentanorprost-trans-13-ene-1,6,9-trione produced a fall in blood pressure of 20 mm Hg and 47 mm Hg lasting 17 and 40 minutes at the doses of 0.5 and 1.0 μg/kg animal body weight, respectively; and 1-hydroxymethyl-11α, 15(S)-dihydroxy-15-(3-propylcyclopentyl)-16,17,18,19,20-pentanorprost-trans-13-ene-1,6,9-trione produced a fall in blood pressure of 20 mm Hg and 35 mm Hg lasting 9 and 23 minutes at the doses of 0.1 and 0.2 μg/kg animal body weight, respectively;

(vi) 1-hydroxymethyl-11α,15(S)-dihydroxy-15-(3-butylcyclopentyl) -16,17,18,19,20-pentanorprost-trans-13-ene-1,6,9-trione; and 1-hydroxymethyl-11α,15(S)-dihydroxy-15-(3-propylcyclopentyl)-16,17,18,19,20-pentanorprost-trans-13-ene-1,6,9-trione produced a 50% inhibition of adenosine diphosphate-induced blood platelet aggregation in platelet-rich plasma of humans at the concentrations of $3.6 \times 10^{-3}$ to $7.2 \times 10^{-2}$ μg/ml and $1.8 \times 10^{-3}$ to $1.8 \times 10^{-2}$ μg/ml, respectively; and (vii) 1-hydroxymethyl-11α,15(S)-dihydroxy-17(S),20-dimethylprost-trans-13-ene-1,6,9-trione, 1-hydroxymethyl-11α,15(S)-dihydroxy-15-(3-butylcyclopentyl)-16,17,18,19,20-pentanorprost-trans-13-ene-1,6,9-trione and 1-hydroxymethyl-11α,15(S)- dihydroxy-15-(3-butylcyclopentyl)-16,17,18,19,20-pentanorprost-trans-13-ene-1,6,9-trione stimulated uterine contraction in the pregnant female rat when administered intravenously on the 20th day of gestation at the doses of 20, 50 and 20 μg/kg animal body weight, respectively.

On the other hand, the compounds of the present invention were confirmed that their toxicities (i.e. $LD_{50}$) were more than 5 mg/kg animal body weight by oral administration. Therefore, the compounds of the present invention may be considered to be sufficiently safe and suitable for medical use.

For example, in a test for acute toxicity in male mice by oral administration, 1-hydroxymethyl-11α,15(S)-dihydroxy-17(S),20-dimethylprost-trans-13-ene-1,6,9-trione caused no deaths in 10 cases at the doses of 5 mg/kg and 10 mg/kg, 1-hydroxymethyl-11α,15(S)-dihydroxy-15-(3-butylcyclopentyl)-16,17,18,19,20-pentanorprost-trans-13-ene-1,6,9-trione caused 2 deaths in 5 cases at the dose of 10 mg/kg, 1-hydroxymethyl-11α,15(S)-dihydroxy-15-(3-propylcyclopentyl)-16,17,18,19,20-pentanorprost-trans-13-ene-1,6,9-trione caused one death in 5 cases at the dose of 5 mg/kg.

Preferred prostaglandin analogues of the present invention are as follows:

2-decarboxy-2-glycoloyl-6-oxo-$PGE_1$,
2-decarboxy-2-glycoloyl-6-oxo-16-methyl-$PGE_1$,
2-decarboxy-2-glycoloyl-6-oxo-17-methyl-$PGE_1$,
2-decarboxy-2-glycoloyl-6-oxo-18-methyl-$PGE_1$,
2-decarboxy-2-glycoloyl-6-oxo-19-methyl-$PGE_1$,
2-decarboxy-2-glycoloyl-6-oxo-16,16-dimethyl-$PGE_1$,
2-decarboxy-2-glycoloyl-6-oxo-16,17-dimethyl-$PGE_1$,
2-decarboxy-2-glycoloyl-6-oxo-16,19-dimethyl-$PGE_1$,
2-decarboxy-2-glycoloyl-6-oxo-16-ethyl-$PGE_1$,
2-decarboxy-2-glycoloyl-6-oxo-17-ethyl-$PGE_1$,
2-decarboxy-2-glycoloyl-6-oxo-16-propyl-$PGE_1$,
2-decarboxy-2-glycoloyl-6-oxo-17-propyl-$PGE_1$,
2-decarboxy-2-glycoloyl-6-oxo-20-methyl-$PGE_1$,
2-decarboxy-2-glycoloyl-6-oxo-16,20-dimethyl-$PGE_1$,
2-decarboxy-2-glycoloyl-6-oxo-17,20-dimethyl-$PGE_1$,
2-decarboxy-2-glycoloyl-6-oxo-16,16,20-trimethyl-$PGE_1$,
2-decarboxy-2-glycoloyl-6-oxo-16-ethyl-20-methyl-$PGE_1$,
2-decarboxy-2-glycoloyl-6-oxo-17-ethyl-20-methyl-$PGE_1$,
2-decarboxy-2-glycoloyl-6-oxo-20-ethyl-$PGE_1$,
2-decarboxy-2-glycoloyl-6-oxo-17-methyl-20-ethyl-$PGE_1$,
2-decarboxy-2-glycoloyl-6-oxo-17,20-diethyl-$PGE_1$,
2-decarboxy-2-glycoloyl-6-oxo-20-butyl-$PGE_1$,
2-decarboxy-2-glycoloyl-6-oxo-20-hexyl-$PGE_1$,
2-decarboxy-2-glycoloyl-6-oxo-15-cyclobutyl-16,17,18,19,20-pentanor-$PGE_1$,
2-decarboxy-2-glycoloyl-6-oxo-15-(1-propylcyclobutyl)-16,17,18,19,20-pentanor-$PGE_1$,
2-decarboxy-2-glycoloyl-6-oxo-15-(1-butylcyclobutyl)-16,17,18,19,20-pentanor-$PGE_1$,
2-decarboxy-2-glycoloyl-6-oxo-15-(1-pentylcyclobutyl)-16,17,18,19,20-pentanor-$PGE_1$,
2-decarboxy-2-glycoloyl-6-oxo-15-(1-hexylcyclobutyl)-16,17,18,19,20-pentanor-$PGE_1$,
2-decarboxy-2-glycoloyl-6-oxo-15-(2-methylcyclobutyl)-16,17,18,19,20-pentaor-$PGE_1$,
2-decarboxy-2-glycoloyl-6-oxo-15-(2-propylcyclobutyl)-16,17,18,19,20-pentanor-$PGE_1$,
2-decarboxy-2-glycoloyl-6-oxo-15-(3-ethylcyclobutyl)-16,17,18,19,20-pentanor-$PGE_1$,
2-decarboxy-2-glycoloyl-6-oxo-15-(3-propylcyclobutyl)-16,17,18,19,20-pentanor-$PGE_1$,
2-decarboxy-2-glycoloyl-6-oxo-15-(2,3,4-triethylcyclobutyl)-16,17,18,19,20-pentanor-$PGE_1$,
2-decarboxy-2-glycoloyl-6-oxo-15-cyclopentyl-16,17,18,19,20-pentanor-$PGE_1$,
2-decarboxy-2-glycoloyl-6-oxo-16-cyclopentyl-17,18,19,20-tetranor-$PGE_1$, 2-decarboxy-2-glycoloyl-6-oxo-17-cyclopentyl-18,19,20-trinor-PGE$_1$,
2-decarboxy-2-glycoloyl-6-oxo-16-cyclopentyl-18,19,20-trinor-PGE$_1$,
2-decarboxy-2-glycoloyl-6-oxo-17-cyclopentyl-19,20-dinor-PGE$_1$,
2-decarboxy-2-glycoloyl-6-oxo-15-(2-pentylcyclopentyl)-16,17,18,19,20-pentanor-PGE$_1$,
2-decarboxy-2-glycoloyl-6-oxo-15-(2,2-dimethylcyclopentyl)-16,17,18,19,20-pentanor-PGE$_1$,
2-decarboxy-2-glycoloyl-6-oxo-15-(3-ethylcyclopentyl)-16,17,18,19,20-pentanor-PGE$_1$,
2-decarboxy-2-glycoloyl-6-oxo-15-(3-propylcyclopentyl)-16,17,18,19,20-pentanor-PGE$_1$,
2-decarboxy-2-glycoloyl-6-oxo-15-(3-butylcyclopentyl)-16,17,18,19,20-pentanor-PGE$_1$,
2-decarboxy-2-glycoloyl-6-oxo-15-(3-tert-butylcyclopentyl)-16,17,18,19,20-pentanor-PGE$_1$,
2-decarboxy-2-glycoloyl-6-oxo-15-(1-methyl-3-propylcyclopentyl)-16,17,18,19,20-pentanor-PGE$_1$,
2-decarboxy-2-glycoloyl-6-oxo-15-(2-methyl-3-propylcyclopentyl)-16,17,18,19,20-pentanor-PGE$_1$,
2-decarboxy-2-glycoloyl-6-oxo-15-(2-methyl-4-propylcyclopentyl)-16,17,18,19,20-pentanor-PGE$_1$,
2-decarboxy-2-glycoloyl-6-oxo-15-cyclohexyl-16,17,18,19,20-pentanor-PGE$_1$,
2-decarboxy-2-glycoloyl-6-oxo-16-cyclohexyl-17,18,19,20-tetranor-PGE$_1$,
2-decarboxy-2-glycoloyl-6-oxo-18-cyclohexyl-19,20-dinor-PGE$_1$,
2-decarboxy-2-glycoloyl-6-oxo-16-methyl-17-cyclohexyl-18,19,20-trinor-PGE$_1$,
2-decarboxy-2-glycoloyl-6-oxo-17-cyclohexyl-19,20-dinor-PGE$_1$,
2-decarboxy-2-glycoloyl-6-oxo-16-methyl-16-cyclohexyl-18,19,20-trinor-PGE$_1$,
2-decarboxy-2-glycoloyl-6-oxo-19-cyclohexyl-20-nor-PGE$_1$,
2-decarboxy-2-glycoloyl-6-oxo-15-(3-ethylcyclohexyl)-16,17,18,19,20-pentanor-PGE$_1$,
2-decarboxy-2-glycoloyl-6-oxo-15-(3-isopropylcyclohexyl)-16,17,18,19,20-pentanor-PGE$_1$,
2-decarboxy-2-glycoloyl-6-oxo-15-(4-methylcyclohexyl)-16,17,18,19,20-pentanor-PGE$_1$,
2-decarboxy-2-glycoloyl-6-oxo-15-(4-ethylcyclohexyl)-16,17,18,19,20-pentanor-PGE$_1$,
2-decarboxy-2-glycoloyl-6-oxo-15-(4-propylcyclohexyl)-16,17,18,19,20pentanor-PGE$_1$,
2-decarboxy-2-glycoloyl-6-oxo-15-(4-butylcyclohexyl)-16,17,18,19,20-pentanor-PGE$_1$,
2-decarboxy-2-glycoloyl-6-oxo-15-(4-tert-butylcyclohexyl)-16,17,18,19,20-pentanor-PGE$_1$,
2-decarboxy-2-glycoloyl-6-oxo-15-(2,6-dimethylcyclohexyl)-16,17,18,19,20-pentanor-PGE$_1$,
2-decarboxy-2-glycoloyl-6-oxo-15-(2,2-dimethylcyclohexyl)-16,17,18,19,20-pentanor-PGE$_1$,
2-decarboxy-2-glycoloyl-6-oxo-15-(2,4,6-trimethylcyclohexyl)-16,17,18,19,20-pentanor-PGE$_1$,
2-decarboxy-2-glycoloyl-6-oxo-16-(1-methylcyclohexyl)-17,18,19,20-tetranor-PGE$_1$,
2-decarboxy-2-glycoloyl-6-oxo-15-cycloheptyl-16,17,18,19,20-pentanor-PGE$_1$,
2-decarboxy-2-glycoloyl-6-oxo-16-cycloheptyl-17,18,19,20-tetranor-PGE$_1$,
2-decarboxy-2-glycoloyl-6-oxo-17-cycloheptyl-18,19,20-trinor-PGE$_1$,
2-decarboxy-2-glycoloyl-6-oxo-16-cycloheptyl-18,19,20-trinor-PGE$_1$,
2-decarboxy-2-glycoloyl-6-oxo-15-phenyl-16,17,18,19,20-pentanor-PGE$_1$,
2-decarboxy-2-glycoloyl-6-oxo-16-phenyl-17,18,19,20-tetranor-PGE$_1$,
2-decarboxy-2-glycoloyl-6-oxo-16-phenyl-18,19,20-tetranor-PGE$_1$,
2-decarboxy-2-glycoloyl-6-oxo-17-phenyl-18,19,20-trinor-PGE$_1$,
2-decarboxy-2-glycoloyl-6-oxo-16-phenoxy-17,18,19,20-tetranor-PGE$_1$,
2-decarboxy-2-glycoloyl-6-oxo-16-(3-chlorophenoxy)-17,18,19,20-tetranor-PGE$_1$,
2-decarboxy-2-glycoloyl-6-oxo-16-(4-chlorophenoxy)-17,18,19,20-tetranor-PGE$_1$,
2-decarboxy-2-glycoloyl-6-oxo-16-(3-trifluoromethylphenoxy)-17,18,19,20-tetranor-PGE$_1$, and cyclodextrin clathrates of such PGE$_1$ analogues.

Particularly preferred prostaglandin analogues of the present invention are:
2-decarboxy-2-glycoloyl-6-oxo-PGE$_1$,
2-decarboxy-2-glycoloyl-6-oxo-16S-methyl-PGE$_1$,
2-decarboxy-2-glycoloyl-6-oxo-17S-methyl-PGE$_1$,
2-decarboxy-2-glycoloyl-6-oxo-17S,20-dimethyl-PGE$_1$,
2-decarboxy-2-glycoloyl-6-oxo-17S-methyl-20-ethyl-PGE$_1$,
2-decarboxy-2-glycoloyl-6-oxo-15-cyclopentyl-16,17,18,19,20-pentanor-PGE$_1$,
2-decarboxy-2-glycoloyl-6-oxo-15-(3-ethylcyclopentyl)-16,17,18,19,20-pentanor-PGE$_1$,
2-decarboxy-2-glycoloyl-6-oxo-15-(3-propylcyclopentyl)-16,17,18,19,20-pentanor-PGE$_1$,
2-decarboxy-2-glycoloyl-6-oxo-15-(3-butylcyclopentyl)-16,17,18,19,20-pentanor-PGE$_1$, and
2-decarboxy-2-glycoloyl-6-oxo-15-(3-tert-butylcyclopentyl)-16,17,18,19,20-pentanor-PGE$_1$.

The following Reference Examples and Examples illustrate the preparation of compounds of the present invention. In the Reference Examples and Examples, 'TLC', 'IR', 'NMR' and 'Mass' represent 'Thin layer chromatography', 'Infrared absorption spectrum', 'Nuclear magnetic resonance' and 'Mass spectrum', respectively. Where solvent ratios are specified in chromatographic separations, the ratios are by volume: the solvents in parentheses in thin layer chromatography show the developing solvents used. Except when specified otherwise, infrared spectra are recorded by the liquid film method and nuclear magnetic resonance spectra are recorded in deuterochloroform (CDCl$_3$) solution.

REFERENCE EXAMPLE 1

Methyl 9α-hydroxy-11α,15(S)-bis(tetrahydropyran-2-yloxy)-17(S),20-dimethyl-prosta-cis-5,trans-13-dienoate.

A mixture of 4.8 g of methyl 9α-acetoxy-11α-(tetrahydropyran-2-yloxy)-15(S)-hydroxy-17(S),20-dimethyl-prosta -cis-5,trans-13-dienoate (this compound is described in Reference Example 3(2) of our Japanese Patent Kokai No. 50-13362.), 1.2 ml of dihydropyran, 17 mg of p-toluene-sulphonic acid and 30 ml of methylene chloride was stirred for 10 minutes at room temperature. Triethylamine was added to the reaction mixture to adjust the pH to 9–10, and the mixture was then concentrated under reduced pressure. The residue was dissolved in 30 ml of methanol, 3.8 g of potassium carbonate was added, and the solution was then stirred for 50 minutes at 45° C. The reaction solution was cooled to −5° C., adjusted to pH 4 by addition of acetic acid, and extracted with 350 ml of ethyl acetate. The extract was washed successively with water, a saturated aqueous solution of sodium bicarbonate, water and a saturated aqueous solution of sodium chloride, dried over anhydrous magnesium sulphate, and concentrated under reduced pressure. The residue was purified by column chromatography on silica gel using a mixture of cyclohexane and ethyl acetate (6:1) as eluent to give 4.7 g of the title compound having the following physical characteristics:

TLC(benzene:ethyl acetate=3:1): Rf=0.25;
Mass: m/e=462, 378, 360, 306.

REFERENCE EXAMPLE 2

Methyl 9α-acetoxy-11α,15(S)-dihydroxy-15-(3-propylcyclopentyl)-16,17,18,19,20-pentanorprosta-cis-5,trans-13-dienoate (less polar isomer and more polar isomer).

A mixture of 12.0 g of methyl 9α-acetoxy-11α-(tetrahydropyran-2-yloxy)-15(S)-hydroxy-15-(3propylcyclopentyl)-16,17,18,19,20-pentanorprosta-cis-5,trans-13-dienoate (this compound is described in Reference Example 7 of our British Patent Specification No. 1,545,213), 200 ml of methanol and 300 mg of pyridine p-toluenesulphonate was stirred for 8 hours at 50° C. After stirring, the mixture was concentrated under reduced pressure, 300 ml of ethyl acetate and 100 ml of a saturated aqueous solution of sodium chloride were added, and the oily layer which separated was dried over anhydrous magnesium sulphate, and then concentrated under reduced pressure.

The residue was purified by column chromatography on silica gel using a mixture of ethyl acetate and cyclohexane (5:1) to give the less polar isomer of the title compound and the more polar isomer of the title compound having the following physical characteristics, respectively:

(i) Less polar isomer
Yield: 3.22 g;
TLC (ethyl acetate): Rf=0.23;
NMR: δ=5.64-5.23 (4H, m), 5.10 (1H, m), 4.02-3.76 (2H, m), 3.67 (3H, s), 2.48 (2H, s), 2.30 (2H, t), 2.05 (3H, s), 2.55-1.03 (22H, m), 0.88 (3H, m);
IR (KBr tablet): ν=3500, 2960, 1735 cm⁻¹;
Mass: m/e=450 (M+), 432, 419, 414, 372, 354, 339, 321, 261, 231, 229.

(ii) More polar isomer
Yield: 3.7 g;
TLC(ethyl acetate): Rf=0.20;
NMR: δ=5.64-5.23 (4H, m), 5.10 (1H, m), 4.02-3.76 (2H, m), 3.67 (3H, s), 2.57 (2H, s), 2.30 (2H, t), 2.60-1.03 (22H, m), 2.05 (3H, s), 0.88 (3H, m);
IR (KBr tablet: ν=3500, 2960, 1735 cm⁻¹;
Mass: m/e=450 (M+), 432, 414, 372, 354, 339, 321, 261, 231, 229.

Using the same procedure the following compounds were obtained from the starting materials indicated:

(a) Methyl 9α-acetoxy-11α,15(S)-dihydroxy-15-(3-butylcyclopentyl) -16,17,18,19,20-pentanorprosta-cis-5,trans-13-dienoate (less polar isomer and more polar isomer)

Starting material: 16.93 g of Methyl 9α-acetoxy-11α-(tetrahydropyran-2-yloxy)-15(S)-hydroxy-15-(3-propylcyclopentyl)-16,17,18,19,20-pentanorprosta-cis-5,trans-13-dienoate (prepared by the procedure described in Reference Example 7 of our British Patent Specification No. 1,545,213)

(i) Less polar isomer
Yield: 3.03 g;
TLC (cyclohexane:ethyl acetate=1:2): Rf=0.7;
NMR δ=5.67 (1H, dd), 5.49 (1H, dd), 5.37 (2H, m), 5.14 (1H, m), 3.91 (2H, m), 3.68 (3H, s), 2.52 (1H, m), 2.31 (2H, t), 2.07 (3H, s), 0.89 (3H, m);
IR (KBr tablet): ν=3480, 1730, 1717, 1248, 972 cm⁻¹;
Mass: m/e=464 (M+), 446, 428, 386, 368.

(ii) More polar isomer
Yield: 2.7 g;
TLC (cyclohexane:ethyl acetate=1:2): Rf=0.6;
NMR: δ=5.64 (1H, dd), 5.47 (1H, dd), 5.34 (2H, m), 5.12 (1H, m), 3.89 (2H, m), 3.67 (3H, s), 2.51 (1H, m), 2.30 (2H, t), 2.06 (3H, s), 0.88 (3H, m);
IR (KBr tablet): ν=3450, 1734, 1247, 978 cm⁻¹;
Mass: m/e=464 (M+), 446, 428, 387, 386, 368.

REFERENCE EXAMPLE 3

Methyl 9α-acetoxy-11α,15(S)-bis(tetrahydropyran-2-yloxy)-15-(3-propylcyclopentyl)-16,17,18,19,20-pentanorprosta-cis-5,trans-13-dienoate.

A mixture of 2.0 g of methyl 9α-acetoxy-11α,15(S)-dihydroxy -15-(3-propylcyclopentyl)-16,17,18,19,20-pentanorprosta -cis-5,trans-13-dienoate [less polar isomer; prepared in Reference Example 2(i)], 1.01 ml of dihydropyran and 22 ml of methylene chloride was stirred whilst cooling with ice. To the mixture a small amount of p-toluenesulphonic acid was added, and then the mixture was allowed to warm to room temperature. A few drops of pyridine were added to the mixture which was then diluted with diethyl ether. The solution obtained was washed with water, and then with a saturated aqueous solution of sodium chloride, dried over anhydrous magnesium sulphate, and concentrated under reduced pressure to give 2.49 g of the title compound having the following physical characteristics:

TLC (ethyl acetate:cyclohexane=1:2): Rf=0.34;
NMR: δ=5.7-5.2 (4H, m), 5.1 (1H, m), 4.7 (2H, m), 4.1-3.2 (6H, m), 3.67 (3H, s), 2.04 (3H, s), 0.9 (3H, m);
IR: ν=1737, 1245, 1121, 976 cm⁻¹;
Mass: m/e=587, 517, 432, 423, 414.

Using the same procedure the following compounds were obtained from the starting materials indicated:

(a) Methyl 9α-acetoxy-11α,15(S)-bis(tetrahydropyran-2-yloxy)-15-(3-butylcyclopentyl)-16,17,18,19,20-pentanorprosta-cis-5,trans-13-dienoate.

Starting material: 2.88 g of methyl 9α-acetoxy-11α,15(S)-dihydroxy-15-(3-butylcyclopentyl)-16,17,18,19,20-pentanorprosta-cis-5,trans-13-dienoate less polar isomer [prepared in Reference Example 2(a) (i).];
Yield: 3.59 g;
TLC (cyclohexane:ethyl acetate=2:1): Rf=0.47;
NMR: δ=5.7-5.3 (4H, m), 5.03 (1H, m), 4.8-4.5 (2H, m), 4.2-3.7 (4H, m), 3.66 (3H, s), 3.47 (2H, m), 2.50 (1H, m), 2.39 (2H, t), 2.04 (3H, s), 0.88 (3H, m);
IR: ν=1738, 1245, 1020, 977 cm⁻¹;
Mass: m/e=548, 530, 517, 499, 446, 386.

REFERENCE EXAMPLE 4

Methyl 9α-hydroxy-11α,15(S)-bis(tetrahydropyran-2-yloxy-15-(3-propylcyclopentyl)-16,17,18,19,20-pentanorprosta-cis-5,trans-13-dienoate.

A mixture of 2.47 g of methyl 9α-acetoxy-11α,15(S)-bis (tetrahydropyran-2-yloxy)-15-(3-propylcyclopentyl)-16,17,18,19,20-pentanorprosta-cis-5,trans-13-dienoate (prepared in Reference Example 3), 1.10 g of anhydrous potassium carbonate and 25 ml of methanol was vigorously stirred for 2.5 hours at 50° C. After stirring, the mixture was concentrated under reduced pressure, the residue was poured into a mixture of ice and 1 N hydrochloric acid, and extracted with ethyl acetate; the extract was washed with water and then with a saturated aqueous solution of sodium chloride, and dried over anhydrous magnesium sulphate. To the solution obtained was added a solution of diazomethane in diethyl ether; the mixture was concentrated under reduced pressure to give 2.48 g of the title compound having the following physical characteristics:

TLC (ethyl acetate:cyclohexane=1:2): Rf=0.20;
NMR: $\delta$=5.7–5.2 (4H, m), 4.7 (2H, m), 4.2–3.3 (7H, m), 3.67 (3H, s), 0.9 (3H, m);
IR: $\nu$=3500, 1741, 1021, 976 cm$^{-1}$;
Mass: m/e=576 (M$^+$), 545, 527, 492, 474, 443.

Using the same procedure the following compounds were obtained from the starting materials indicated:

(a) Methyl 9α-hydroxy-11α,15(S)-bis(tetrahydropyran-2-yloxy)-15-(3-butylcyclobutyl)-16,17,18,19,20-pentanorprosta-cis-5,trans-13-dienoate.

Starting material: 3.58 g of methyl 9α-acetoxy-11α,15(S)-bis(tetrahydropyran-2-yloxy)-15-(3-butylcyclopentyl)-16,17,18,19,20-pentanorprosta-cis-5,trans-13dienoate [prepared in Reference Example 3(a)];

Yield: 2.92 g;
TLC (ethyl acetate:cyclohexane=1:2): Rf=0.30;
NMR: $\delta$=5.6–5.3 (4H, m), 4.7 (2H, m), 4.2–4.0 (2H, m), 3.75 (2H, m), 3.67 (3H, s), 3.48 (2H, m), 2.32 (2H, t), 0.88 (3H, m);
IR: $\nu$=3500, 1739, 1022, 976 cm$^{-1}$;
Mass: m/e=506, 488, 457, 404, 386.

(b) Methyl 9α-hydroxy-11α,15(S)-bis(tetrahydropyran-2-yloxy)-15-cyclopentyl-16,17,18,19,20-pentanorprosta-cis-5,trans-13-dienoate.

Starting material: 2.04 g of methyl 9α-acetoxy-11α,15(S)-bis(tetrahydropyran-2-yloxy)-15-cyclopentyl-16,17,18,19,20-pentanorprosta-cis-5,trans-13-dienoate (this compound is described in Reference Example 29 of our U.S. Pat. No. 4,034,003);

Yield: 1.61 g;
TLC (cyclohexane:ethyl acetate=1:1): Rf=0.33;
NMR: $\delta$=5.6–5.25 (4H, m), 4.70 (2H, m), 4.1 (2H, m), 3.83 (3H, m), 3.66 (3H, s), 3.46 (2H, m);
IR: $\nu$=3650–3200, 2950, 2860, 1740, 1450, 1440, 1370, 1350, 1240 cm$^{-1}$;
Mass: m/e=485, 450, 432, 419, 414, 401, 381, 360, 348, 330, 297, 276.

REFERENCE EXAMPLE 5

Methyl 5-bromo-6,9α-epoxy-11α,15(S)-bis(tetrahydropyran-2-yloxy)-15-(3-propylcyclopentyl)-16,17,18,19,20-pentanorprost-trans-13-enoate.

To a mixture of 2.48 g of methyl 9α-hydroxy-11α,15(S)-bis(tetrahydropyran-2-yloxy)-15-(3-propylcyclopentyl)-16,17,18,19,20-pentanorprosta-cis-5,trans-13-dienoate (prepared in Reference Example 4), 31 ml of methylene chloride, and 3.95 ml of tetrahydrofuran, 0.85 g of N-bromosuccinimide was added all at once at room temperature, and the solution was stirred for 1 hour. The solution was diluted with 100 ml of diethyl ether, washed with water, and a saturated aqueous solution of sodium chloride, concentrated under reduced pressure and purified by column chromatography on silica gel using a mixture of cyclohexane and ethyl acetate (4:1) as an eluent to give 2.30 g of the title compound having the following physical characteristics:

NMR: $\delta$=5.7–5.2 (2H, m), 4.7 (2H, m), 4.5 (1H, m), 3.67 (3H, s), 0.9 (3H, m);
IR: $\nu$=1741, 1022, 982 cm$^{-1}$;
Mass: m/e=555, 553, 541, 539, 523, 521, 470, 468, 452, 450, 426, 424.

Using the same procedure the following compounds were obtained from the starting materials indicated: (a) Methyl 5-bromo-6,9α-epoxy-11α,15(S)-bis(tetrahydropyran-2-yloxy)-15-(3-butylcyclopentyl)-16,17,18,19,20-pentanorprost-trans-13-enoate.

Starting material: 2.90 g of methyl 9α-hydroxy-11α,15(S)-bis(tetrahydropyran-2-yloxy)-15-(3-butylcyclopentyl)-16,17,18,19,20-pentanorprosta-cis-5,trans-13-dienoate [prepared in Reference Example 4(a)]:

Yield: 3.14 g;
NMR: $\delta$=5.7–5.25 (2H, m), 4.8–4.5 (2H, m), 4.4–3.7 (7H, m), 3.69 (3H, s), 3.48 (2H, m), 0.89 (3H, m);
IR: $\nu$=1738, 1018, 977 cm$^{-1}$;
Mass: m/e=568, 566, 555, 553, 535, 533, 484, 482, 466, 464, 440, 438, 403.

(b) Methyl 5-bromo-6,9α-epoxy-11α,15(S)-bis(tetrahydropyran-2-yloxy)-15-cyclopentyl-16,17,18,19,20-pentanorprost-trans-13-enoate.

Starting material: 1.60 g of methyl 9α-hydroxy-11α,15(S)-bis(tetrahydropyran-2-yloxy)-15-cyclopentyl-16,17,18,19,20-pentanorprosta-cis-5,trans-13-dienoate [prepared in Reference Example 4(b)];

Yield: 1.97 g;
TLC (cyclohexane:ethyl acetate=1:1): Rf=0.6;
NMR: $\delta$=5.68–5.3 (2H, m), 4.7 (2H, m), 4.55 (1H, m), 3.68 (3H, s), 2.35 (2H, t);
IR: $\nu$=3600–3200, 2940, 2850, 1735, 1440, 1350, 1320, 1260, 1240, 1200, 1130 cm$^{-1}$;
Mass: m/e=428, 426, 408, 384, 382, 377, 359, 357, 347, 315, 311, 304, 297.

(c) Methyl 5-bromo-6,9α-epoxy-11α,15(S)-bis(tetrahydropyran-2-yloxy)-17(S),20-dimethyl-prost-trans-13-enoate.

Starting material: 4.35 g of methyl 9α-hydroxy-11α,15(S)-bis(tetrahydropyran-2-yloxy)-17(S),20-dimethylprosta-cis-5,trans-13-dienoate (prepared in Reference Example 1);

Yield: 5.8 g;
TLC (cychohexane:ethylacetate=2:1): Rf=0.64;
NMR: $\delta$=5.6–5.1 (2H, m), 5.0–4.3 (3H, m), 4.3–3.0 (8H, m), 3.6 (3H, s);
IR: $\nu$=2930, 2860, 1740, 1435, 1350, 1240, 1120, 1070, 1030, 1015, 970 cm$^{-1}$;
Mass: m/e=456, 438, 412, 377, 346.

Reference Example 6

5-Bromo-6,9α-epoxy-11α,15(S)-bis(tetrahydropyran-2-yloxy)-15-(3-propylcyclopentyl)-16,17,18,19,20-pentanorprost-trans-13-3-en-1-al.

To a solution of 2.30 g of methyl 5-bromo-6,9α-epoxy-11α,15(S)-bis(tetrahydropyran-2-yloxy)-15-(3-propylcyclopentyl)-16,17,18,19,20-pentanorprost-trans-13-enoate (prepared in Reference Example 5) in 35 ml of toluene cooled to −78° C., 2.6 ml of a 25% (w/v) solution of diisobutyl aluminium hydride in toluene was added dropwise.

The reaction mixture was stirred for 30 minutes, 0.7 ml of methanol was carefully added, and the temperature of the mixture was raised to 0° C. 1.8 ml of water was then added and the mixture was stirred vigorously. After an addition of anhydrous magnesium sulphate, the mixture was filtered, and the filtrate was concentrated under reduced pressure. The residue obtained was purified by column chromatography on silica gel using a mixture of cyclohexane and ethyl acetate (3:1) as an eluent to give 2.1 g of the title compound having the following physical characteristics:

NMR: $\delta = 9.8$ (1H, t), 5.7–5.2 (2H, m), 4.7 (2H, m), 4.5 (1H, m), 0.9 (3H, m);
IR: $\nu = 2725, 1725, 980$ cm$^{-1}$;
Mass: m/e=440, 438, 422, 420, 396, 394.

Using the same procedure the following compounds were obtained from the starting materials indicated:

(a) 5-Bromo-6,9α-epoxy-11α,15(S)-bis(tetrahydropyran-2-yloxy)-15-(3-butylcyclopentyl)-16,17,18,19,20-pentanorprost-trans-13-en-1-al.

Starting material: 3.13 g of methyl 5-bromo-6,9α-epoxy-11α,15(S)-bis(tetrahydropyran-2-yloxy)-15-(3-butylcyclopentyl)-16,17,18,19,20-pentanorprost-trans-13-enoate [prepared in Reference Example 5(a)];
Yield: 2.71 g;
NMR: $\delta = 9.78$ (1H, t), 5.7–5.2 (2H, m), 4.68 (2H, m), 4.54 (1H, m), 4.47 (2H, m), 4.2–4.1 (1H, m), 4.1–3.7 (5H, m), 2.5 (2H, t), 0.89 (3H, m);
IR: $\nu = 2730, 1726, 1022, 980$ cm$^{-1}$;
Mass: m/e=454, 452, 410, 408.

(b) 5-Bromo-6,9α-epoxy-11α,15(S)-bis(tetrahydropyran-2-yloxy)-15-cyclopentyl-16,17,18,19,20-pentanorprost-trans-13-en-1-al.

Starting material: 1.97 g of methyl 5-bromo-6,9α-epoxy-11α,15(S)-bis(tetrahydropyran-2-yloxy)-15cyclopentyl-16,17,18,19,20-pentanorprost-trans-13-enoate (prepared in Reference Example 5(b)):
Yield: 1.43 g;
TLC(cyclohexane:ethyl acetate=2:1): Rf=0.3;
NMR: $\delta = 9.98$ (1H, t), 5.68–5.3 (2H, m), 4.7 (2H, m), 4.55 (1H, m), 2.5 (2H, t);
IR: $\nu = 3650-3200, 2950, 2870, 1725, 1450, 1370, 1350, 1320, 1240, 1200, 1130$ cm$^{-1}$;
Mass: m/e=483, 431, 429, 398, 396, 380, 354, 352, 345, 329, 327, 317.

(c) 5-Bromo-6,9α-epoxy-11α,15(S)-bis(tetrahydropyran-2-yloxy)-17(S),20-dimetnylprost-trans-13-en-1-al.

Starting material: 4.95 g of methyl 5-bromo-6,9α-epoxy-11α,15(S)-bis(tetrahydropyran-2-yloxy)-17(S),20-dimethylprost-trans-13-enoate [prepared in Reference Example 5(c)];
Yield: 3.96 g;
TLC(cyclohexane:ethyl acetate=2:1): Rf=0.46;
NMR: $\delta = 9.7-9.6$ (1H, m), 5.7–5.1 (2H, m), 4.8–3.1 (11H, m);
IR: $\nu = 2920, 2860, 2700, 1725, 1440, 1370, 1340, 1120, 1070, 1010, 970$ cm$^{-1}$;
Mass: m/e=426, 408, 382, 347.

REFERENCE EXAMPLE 7

1-Hydroxy-1-(2,4-dioxa-3-methylhexyl)-5-bromo-6,9α-epoxy-11α,15(S)-bis(tetrahydropyran-2-yloxy)-15-(3-propylcyclopentyl)-16,17,18,19,20-pentanorprost-trans-13-ene.

To a solution of 3.06 g of (2,4-dioxa-3-methylhexyl)-tributyl stannane (this compound is described in J. Am. Chem. Soc., 100, 1481 (1978)) in 40 ml of tetrahydrofuran cooled to −78° C., was added dropwise 4.9 ml of a 1.6 M solution of n-butyl lithium in hexane over a period of 7 minutes. After stirring for 10 minutes at the same temperature, to the solution obtained was added dropwise a solution of 1.63 g of 5-bromo-6,9α-epoxy-11α,15(S)-bis(tetrahydropyran-2-yloxy)-15-(3-propylcyclopentyl)-16,17,18,19,20-pentanorprost-trans-13-en-1-al (prepared in Reference Example 6) in 12 ml of tetrahydrofuran over a period of 10 minutes with stirring. After stirring for 30 minutes, the solution was poured into aqueous ammonia, and extracted with diethyl ether. The extract was washed with water and a saturated aqueous solution of sodium chloride, dried over magnesium sulphate, and concentrated under reduced pressure; the residue was purified by column chromatography on silica gel using a mixture of cyclohexane and ethyl acetate (1:1) as an eluent to give 1.61 g of the title compound having the following physical characteristics:

NMR: $\delta = 4.8$ (2H, m), 4.7 (3H, m), 1.3 (3H, d), 1.2 (3H, t), 0.9 (3H, m);
IR: $\nu = 3480, 1132, 1020, 980$ cm$^{-1}$;
Mass: m/e=498, 496, 454, 452.

Using the same procedure the following compounds were obtained from the starting materials indicated:

(a) 1-Hydroxy-1-(2,4-dioxa-3-methylhexyl)-5-bromo-6,9α-epoxy-11α,15(S)-bis(tetrahydropyran-2-yloxy)-15-(3-butylcyclopentyl)-16,17,18,19,20-pentanorprost-trans-13-ene.

Starting material: 2.09 g of 5-bromo-6,9α-epoxy-11α,15(S)-bis(tetrahydropyran-2yloxy)-15-(3-butylcyclopentyl)-16,17,18,19,20-pentanorprost-trans-13-en-1-al [prepared in Reference Example 6(a)];
Yield: 1.86 g;
NMR: $\delta = 5.7-5.2$ (2H, m), 4.8–4.5 (3H, m), 4.2–4.1 (1H, m), 1.33 (3H, d), 1.22 (3H,t), 0.88 (3H, m);
IR: $\nu = 3490, 1135, 1020, 980$ cm$^{-1}$;
Mass: m/e=698, 696, 613, 611, 596, 594, 502, 500, 447, 445, 444, 442, 468, 466.

(b) 1-Hydroxy-1-(2,4-dioxa-3-methylhexyl)-5-bromo-6,9α-epoxy-11α,15(S)-bis(tetrahydropyran-2-yloxy)-15-cyclopentyl-16,17,18,19,20-pentanorprost-trans-13-ene Starting material: 1.43 g of 5-bromo-6,9α-epoxy-11α,15(S)-bis(tetrahydropyran-2-yloxy)-15-cyclopentyl-16,17,18,19,20-pentanorprost-trans-13-en-1-al [prepared in Reference Example 6(b)];
Yield: 1.46 g;
TLC(cyclohexane:ethyl acetate=1:1): Rf=0.25;
NMR: $\delta = 5.68-5.3$ (2H, m), 4.7 (2H,m), 4.55 (1H, m), 4.15 (1H, m), 1.35 (3H, d), 1.22 (3H, t);
IR: $\nu = 3650-3200, 2940, 2870, 1440, 1380, 1340, 1260, 1240, 1200, 1130$ cm$^{-1}$;

Mass: m/e=455, 453, 440, 438, 411, 409, 373, 342, 340, 314, 312.

(c) 1-Hydroxy-1-(2,4-dioxa-3-methylhexyl)-5-bromo-6,9α-epoxy-11α,15(S)-bis(tetrahydropyran-2-yloxy)-17(S),20-dimethylprost-trans-13-ene.

Starting material: 3.88 g of 5-bromo-6,9α-epoxy-11α,15(S)-bis(tetrahydropyran-2-yloxy)-17(S),20-dimethylprost-trans-13-en-1-al [prepared in Reference Example 6(c)];

Yield: 3.62 g;

TCL(cyclohexane:ethyl acetate=1:1): Rf=0.43;

NMR: δ=5.7–5.2 (2H, m), 5.1–3.1 (17H,m);

IR: ν=3480, 2920, 2860, 1440, 1380, 1130, 1020, 975 cm$^{-1}$;

Mass: m/e=484, 440, 405.

REFERENCE EXAMPLE 8

1,9α-Dihydroxy-1-(2,4-dioxa-3-methylhexyl)-11α,15(S)-bis(tetrahydropyran-2-yloxy)-15-(3-propylcyclopentyl)-16,17,18,19,20-pentanorprost-trans-13en-6-one.

A mixture of 1.59 g of 1-hydroxy-1-(2,4-dioxa-3-methylhexyl)-5-bromo-6,9α-epoxy-11α,15(S)-bis(tetrahydropyran-2-yloxy)-15-(3-propylcyclopentyl)-16,17,18,19,20-pentanorprost-trans-13-ene (prepared in Reference Example 7), 3.4 ml of 1,5-diazabicyclo[5,4,-0]undecene-5 and 2.8 ml of toluene was heated at 50° C. for 14 hours, and then at 80° C. for 5 hours. The mixture was then cooled in an ice bath, diluted with cold diethyl ether and then shaken with cooled 1 N hydrochloric acid. The oily layer obtained was washed with water, a saturated aqueous solution of sodium bicarbonate and a saturated aqueous solution of sodium chloride, dried over anhydrous magnesium sulphate, and then concentrated under reduced pressure. The residue was purified by column chromatography on silica gel using a mixture of cyclohexane and ethyl acetate (1:1) as an eluent to give 1.14 g of the title compound having the following physical characteristics:

TLC(ethyl acetate:cyclohexane=1:1): Rf=0.05;

NMR: δ=5.8–5.2 (2H, m), 4.8–4.4 (3H, m), 0.9 (3H, m);

IR: ν=3470, 1708, 1130, 1020, 977 cm$^{-1}$;

Mass: m/e=603, 545, 501, 416, 407.

Using the same procedure the following compounds were obtained from the starting materials indicated:

(a) 1,9α-Dihydroxy-1-(2,4-dioxa-3-methylhexyl)-11α,15(S)-bis(tetrahydropyran-2-yloxy)-15-(3-butylcyclopentyl)-16,17,18,19,20-pentanorprost-trans-13-en-6-one.

Starting material: 1.84 g of 1-hydroxy-1-(2,4dioxa-3-methylhexyl)-5-bromo-6,9α-epoxy-11α,15(S)-bis(-tetrahydropyran-2-yloxy)-15-(3-butylcyclopentyl)-16,17,18,19,20-pentanorprost-trans-13-ene [prepared in Reference Example 7(a)];

Yield: 1.02 g;

TLC(cyclohexane:ethyl acetate=1:1): Rf=0.09;

NMR: δ=5.5 (1H, m), 5.3 (1H, m), 4.7–4.4 (6H, m), 4.1–3.2 (12H, m), 1.18 (3H, t), 0.87 (3H,m);

IR: ν=3470, 1710, 1132, 1018, 976 cm$^{-1}$;

(b) 1,9α-Dihydroxy-1-(2,4-dioxa-3-methylhexyl)-11α,15(S)-bis(tetrahydropyran-2-yloxy)-15-cyclopentyl-16,17,18,19,20-pentanorprost-trans-13-en-6-one.

Starting material: 1.45 g of 1-hydroxy-1-(2,4-dioxa-3-methylhexyl)-5-bromo-6,9-epoxy-11α,15(S) -bis(-tetrahydropyran-2-yloxy)-15-cyclopentyl-16,17,18,19,20-pentanorprost-trans-13-ene [prepared in Reference Example 7(b)]:

Yield: 920 mg;

TLC(cyclohexane:ethyl acetate=1:1): Rf=0.1;

NMR: δ=5.7–5.2 (2H, m), 4.7 (2H, m), 4.55 (1H, m), 1.26 (3H, d), 1.2 (3H, t);

IR: ν=3650–3100, 2940, 2860, 1740, 1710, 1440, 1370, 1340, 1240, 1200, 1130 cm$^{-1}$;

Mass: m/e=561, 533, 521, 503, 475, 459, 433, 419, 407, 374, 356, 348.

(c) 1,9α-Dihydroxy-1-(2,4-dioxa-3-methylhexyl)-11α,15(S)-bis(tetrahydropyran-2-yloxy)-17(S),20-dimethylprost-trans-13-en-6-one.

Starting material: 3.62 g of 1-hydroxy-1-(2,4-dioxa-3-methylhexyl)-5-bromo-6,9α-epoxy-11α,15(S)-bis(-tetrahydropyran-2-yloxy)-17(S),20-dimethylprost-trans-13-ene [prepared in Reference Example 7(c)];

Yield: 1.94 g;

TLC(cyclohexane:ethyl acetate=2:1): Rf=0.08;

NMR: 5.7–5.1 (2H, m), 4.8–4.3 (4H, m), 4.3–3.0 (1H, m);

IR: ν=3450, 2920, 2860, 1700, 1440, 1370, 1340, 1120, 1015, 970 cm$^{-1}$;

Mass: m/e=591, 563, 533, 489, 461, 449, 405.

REFERENCE EXAMPLE 9

1-(2,4-Dioxa-3-methylhexyl)-11α,15(S)-bis(tetrahydropyran-2-yloxy)-15-(3-propylcyclopentyl)-16,17,18,19,20-pentanorprost-trans-13-ene-1,6,9-trione.

To Collins reagent (a mixture of 83 ml of methylene chloride, 5.5 ml of pyridine, 3.36 g of chromium trioxide and 17.5 g of Celite) was added a solution of 1.1 g of 1,9α-dihydroxy-1-(2,4-dioxa-3-methylhexyl)-11α,15(S)-bis(tetrahydropyran-2-yloxy)-15-(3-propylcyclopentyl)-16,17,18,19,20-pentanorprost-trans-13-en-6-one (prepared in Reference Example 8) in 13 ml of methylene chloride at room temperature. After stirring for 20 minutes, 25 g of sodium bisulphate was added to the mixture, which was then stirred for 10 minutes, and filtered through anhydrous magnesium sulphate; the filtrate was concentrated under reduced pressure and the residue purified by column chromatography on silica gel using a mixture of cyclohexane and ethyl acetate (3:1) as an eluent to give 0.40 g of the title compound having the following physical characteristics:

TLC(cyclohexane:ethyl acetate=1:1): Rf=0.33;

NMR: δ=5.8–5.3 (2H, m), 4.78 (1H, q), 4.7 (2H, m), 4.08 (2H, s), 3.57 (2H, q), 1.33 (3H, d), 1.17 (3H, t), 0.9 (3H, m);

IR: ν=1742, 1717, 1115, 1080, 1037, 1023, 976 cm$^{-1}$;

Mass: m/e=617, 515, 458, 430, 421, 412, 404, 386.

Using the same procedure the following compounds were obtained from the starting materials indicated:

(a) 1-(2,4-Dioxa-3-methylhexyl)-11α,15(S)-bis(tetrahydropyran-2-yloxy)-15-(3-butylcyclopentyl)-16,17,18,19,20-pentanorprost-trans-13-ene-1,6,9-trione.

Starting material: 0.99 g of 1,9α-dihydroxy-1-(2,4-dioxa-3-methylhexyl)-11α,15(S)-bis(tetrahydropyran-2-yloxy)-15-(3-butylcyclopentyl)-16,17,18,19,20-pentanorprost-trans-13-en-6 one [prepared in Reference Example 8(a)];

Yield: 0.52 g;

TLC(cyclohexane:ethyl acetate=1:1): Rf=0.36;

NMR: δ=5.6 (1H, m), 5.4 (1H, m), 4.83 (3H, m), 4.78 (1H, g), 4.8–4.6 (2H, m), 4.7–4.4 (4H, m), 4.2–4.0 (1H, m), 4.09 (2H, d), 1.34 (3H, d), 1.19 (3H, t), 0.88 (3H, t);

IR: ν=1743, 1715, 973 cm$^{-1}$;

Mass: m/e=575, 546, 529, 472, 444, 426, 421, 418, 400.

(b) 1-(2,4-Dioxa-3-methylhexyl)-11α,15(S)-bis(tetrahydropyran-2-yloxy)-15-cyclopentyl-16,17,18,19,20-pentanorprost-trans-13-ene-1,6,9-trione.

Starting material: 910 mg of 1,9α-dihydroxy-1-(2,4-dioxa-3-methylhexyl)-11α,15(S)-bis-(tetrahydropyran-2-yloxy)-15-cyclopentyl-16,17,18,19,20-pentanorprost-trans-13-en-6-one [prepared in Reference Example 8(b)];
Yield: 448 mg;
TLC(cyclohexane:ethyl acetate=1:2): Rf=0.5;
NMR: δ=5.7–5.3 (2H, m), 4.78–4.65 (3H, m), 4.1 (1H, d), 1.35 (3H, d), 1.2 (3H, t);
IR: ν=3650–3100, 2940, 2870, 1740, 1715, 1450, 1380, 1350, 1260, 1130 $cm^{-1}$;
Mass: m/e=575, 519, 490, 473, 421, 388, 370, 362, 353, 344.

(c) 1-(2,4-Dioxa-3-methylhexyl)-11α,15(S)-bis(tetrahydropyran-2-yloxy)-17(S),20-dimethylprost-trans-13-ene-1,6,9-trione.

Starting material: 1.94 g of 1,9α-dihydroxy-1-(2,4-dioxa-3-methylhexyl)-11α,15(S)-bis(tetrahydropyran-2-yloxy)-17(S),20-dimethylprost-trans-13-en-6-one [prepared in Reference Example 8(c)];
Yield: 1.19 g;
TLC(cyclohexane:ethyl acetate=1:2): Rf=0.72;
NMR: δ=5.7–5.1 (2H, m), 4.9–4.4 (3H, m), 4.4–3.1 (8H, m), 4.0 (2H, s);
IR: ν=2920, 2860, 1745, 1720, 1440, 1370, 1120, 1070, 1030, 1015, 970 $cm^{-1}$;
Mass: m/e=591, 533, 418.

EXAMPLE 1

1-Hydroxymethyl-11α,15(S)-dihydroxy-15-(3-propylcyclopentyl)-16,17,18,19,20-pentanorprost-trans-13-ene-1,6,9-trione. [i.e. 2-Decarboxy-2-glycoloyl-6-oxo-15(S)-(3-propylcyclopentyl)-16,17,18,19,20-pentanor-PGE$_1$]

A mixture of 0.38 g of 1-(2,4-dioxa-3-methylhexyl)-11α,15(S)-bis(tetrahydropyran-2-yloxy)-15-(3-propylcyclopentyl)-16,17,18,19,20-pentanorprost-trans-13-ene-1,6,9-trione (prepared in Reference Example 9), 6 ml of 65% v/v aqueous acetic acid and 0.6 ml of tetrahydrofuran was heated at 50° C. for 4 hours with stirring. The mixture was diluted with 120 ml of ethyl acetate, washed with water, a saturated aqueous solution of sodium bicarbonate and a saturated aqeous solution of sodium chloride, dried over anhydrous magnesium sulphate, concentrated under reduced pressure and the residue purified by column chromatography on silica gel using a mixture of cyclohexane and ethyl acetate (2:1) as an eluent; the product obtained was recrystallized from a mixture of cyclohexane and ethyl acetate (1:2) to give 0.111 g of the title compound having the following physical characteristics:

Melting point: 88°–91° C.;
TLC(ethyl acetate:formic acid=80:1): Rf=0.16;
NMR: δ=5.60 (2H, m), 4.24 (2H, s), 4.12 (1H, m), 3.86 (1H, m), 2.79 (1H, dd), 0.88 (3H, m);
IR(KBr tablet): ν=3470, 2860, 1748, 1730, 1707, 1081, 972 $cm^{-1}$;
Mass: m/e=422, 404, 386, 373, 355, 328, 309, 293.

Using the same procedure the following compounds were obtained from the starting materials indicated:

(a) 1-Hydroxymethyl-11α,15(S)-dihydroxy-15-(3-butylcyclopentyl)-16,17,18,19,20-pentanorprost-trans-13-ene-1,6,9-trione. [i.e. 2-Decarboxy-2-glycoloyl-6-oxo15(S)-(3-butylcyclopentyl)-16,17,18,19,20-pentanor-PGE$_1$.]

Starting material: 0.51 g of 1-(2,4-dioxa-3-methylhexyl)-11α,15(S)-bis(tetrahydropyran-2-yloxy)-15-(3-butylcyclopentyl)-16,17,18,19,20-pentanorprost-trans-13-ene-1,6,9-trione [prepared in Reference Example 9(a)];
Yield: 0.21 g;
Melting point: 95°–96° C.;
TLC(ethyl acetate:formic acid=80:1): Rf=0.21;
NMR: δ=5.60 (2H, m), 4.24 (2H, s), 4.12 (1H, m), 3.86 (1H, m), 2.79 (1H, dd), 0.88 (3H, m);
IR (KBr tablet): ν=3460, 1748, 1732, 1710, 1288, 970 $cm^{-1}$;
Mass: m/e=418, 400, 382, 369, 293, 257, 229.

(b) 1-Hydroxymethyl-11α,15(S)-dihydroxy-15-cyclopentyl-16,17,18,19,20-pentanorprost-trans-13-ene-1,6,9-trione [i.e. 2-Decarboxy-2-glycoloyl-6-oxo-15(S)-cyclopentyl-16,17,18,19,20-pentaor-PGE$_1$.]

Starting material: 432 mg of 1-(2,4-dioxa-3-methylhexyl)-11α,15(S)-bis(tetrahydropyran-2-yloxy)-15-cyclopentyl-16,17,18,19,20-pentanorprost-trans-13-ene-1,6,9-trione [prepared in Reference Example 9(b)];
Yield: 120 mg;
Melting point: 81° C.-83° C.;
TLC(ethyl acetate:formic acid=80:1): Rf=0.08;
NMR: δ=5.57 (2H, m), 4.23 (2H,s), 4.1 (2H, q), 3.95 (1H, t), 3.2–2.2 (12H, m), 2.05–1.0 (14H, m);
IR (KBr tablet): ν=3600–3100, 2950, 2860, 1760, 1730, 1710, 1450, 1400, 1070 $cm^{-1}$;
Mass: m/e=362, 344, 331, 326, 315, 293, 257, 229, 201, 148.

(c) 1-Hydroxymethyl-11α,15(S)-dihydroxy-17(S),20-dimethylprost-trans-13-ene-1,6,9-trione, [i.e. 2-Decarboxy-2-glycoloyl-17(S),-20-dimethyl-PGE$_1$,].

Starting material: 1.19 g of 1-(2,4-dioxa-3-methylhexyl)-11α,15(S)-bis(tetrahydropyran-2-yloxy)-17(S),20-dimethylprost-trans-13-ene-1,6,9-one [prepared in Reference Example 9(c)];
Yield: 267 mg;
TLC(ethyl acetate:formic acid=80:1):Rf=0.20;
NMR: δ=5.75–5.35 (2H, m), 4.4–3.9 (2H, m), 4.22 (2H, m), 2.77 (1H, dd);
IR: ν=3400, 2920, 2860, 1740, 1715, 1400, 1370, 1070, 970 $cm^{-1}$;
Mass: m/e=410 (M+), 392, 374, 361, 356, 143.

EXAMPLE 2

α-Cyclodextrin clathrate of 1-hydroxymethyl-11α,15(S)-dihydroxy-17(S),20-dimethylprost-trans-13-ene-1,6,9-trione.

A solution of 23.4 mg of 1-hydroxymethyl-11α,15(S)-dihydroxy-17(S),20-dimethylprost-trans-13-ene-1,6,9-trione [prepared as described in Example 1(c)] in 2.9 ml of ethanol was added to a solution of 672 mg of 60-cyclodextrin in 6 ml of water and the mixture was stirred at room temperature. The mixture was concentrated under reduced pressure to give 609 mg of the α-cyclodextrin clathrate of the compound specified in the title. The content of prostaglandin analogue in the product was 2.9% by weight.

α-Cyclodextrin clathrates of the compounds of Examples 1, 1(a) and 1(b) were prepared in a similar manner.

The present invention includes within its scope pharmaceutical compositions which comprise at least one prostaglandin analogue of general formula (IV) or cyclodextrin clathrate thereof, together with a pharmaceutical carrier or coating.

In clinical practice, for the treatment of cytodamage or gastric ulceration, the compounds of the present invention will normally be administered systemically or partially; usually by oral or parenteral (e.g. intravenous, subcutaneous or intramuscular) administration.

Solid compositions for oral administration include compressed tablets, pills, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents, e.g. lubricating agents such as magnesium stearate, and disintegrating agents, such as cellulose calcium gluconate. The tablets or pills may, if desired, be made into enteric film-coated or gastric film-coated tablets or pills, such as sugar-coated, gelatin-coated, hydroxypropylcellulose-coated or hydroxypropylmethylcellulose phthalate-coated tablets or pills; two or more layers may be used.

The compositions for oral administration also include capsules of absorbable material such as gelatin, containing one or more of the active substances with or without the addition of diluents or excipients.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise at least one compound of the present invention.

Preparations according to the invention for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, and Polysorbate 80 (registered Trade Mark). These compositions may also include adjuvants such as preserving, wetting, emulsifying and dispersing agents. They may be sterilized, for example, by filtration through a bateria-retaining filter, by incorporation of sterilizing agents in the compositions or by irradiation. They may also be manufactured in the form of steril solid compositions which can be dissolved in sterile water or some other sterile injectable medium immediately before use.

Other compositions include, for parenteral administration, liquids for external use, and endermic liniments such as ointments; suppositories for rectal administration; and pessaries for vaginal administration. Such compositions are prepared by known methods.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dose to be administered is determined depending upon, for example, age, symptoms, the desired therapeutic effects, the route of administration, and the duration of the treatment.

In the human adult, the doses per person are generally between 0.1 and 100 μg, preferably between 1 and 50 μg by oral administration, and between 0.01 and 50 μg, preferably between 0.1 and 20 μg by parenteral administration in the treatment of cyto-damage, and can be administered up to several times per day. The doses per person are generally between 0.5 μg and 1 mg by oral, intravenous and subcutaneous administration in the treatment of gastric ulceration, and can be administered up to several times per day.

As mentioned above, the doses to be used depend on various conditions. Therefore, there may be cases in which doses greater than the ranges specified above, or lower than the ranges specified above, may be used.

The following Examples illustrate pharmaceutical compositions according to the invention.

EXAMPLE 3

3 mg. of 1-hydroxymethyl-11α,15(S)-dihydroxy-17(S),20-dimethylprost-trans-13-ene-1,6,9-trione, 100 mg. of magnesium stearate, 20 mg. of silicon dioxide, 10 mg. of talc, 200 mg. of cellulose calcium gluconate and 9.667 g. of microcrystalline cellulose were mixed and punched out in known manner to obtain 100 tablets each containing 30 μg. of the active ingredient.

EXAMPLE 4

3 mg. of 1-hydroxymethyl-11α,15(S)-dihydroxy-17(S),20-dimethylprost-trans-13-ene-1,6,9-trione and 20.997 g. of lactose were mixed and the powder obtained was machine filled into 100 No. 2 hard capsules each containing 30 μg. of the active ingredient.

EXAMPLE 5

A solution of 30 mg. of 1-hydroxymethyl-11α,15(S)-dihydroxy-17(S),20-dimethylprost-trans-13-ene-1,6,9-trione in 10 ml of chloroform was added to 100 ml of MCT (registered Trade Mark; a mixture of triglycerides of fatty acids containing 8 to 10 carbon atoms) and the solution was mixed. After removing chloroform under reduced pressure, the residue was machine filled into 100 soft capsules to give capsules each containing 30 μg. of the active ingredient.

EXAMPLE 6

6 mg. of α-cyclodextrin clathrate of 1-hydroxymethyl-11α,15(S)-dihydroxy-17(S),20-dimethylprost-trans-13-ene-1,6,9-trione (content of active agent: 500 μg.) was dissolved in 300 ml of distilled water for injection. The solution was sterilized in conventional manner and placed in 3 ml portions in 5 ml ampoules to obtain 100 ampoules each containing 5 μg. of the active ingredient.

EXAMPLE 7

Tablets, hard capsules, soft capsules and injectable solutions were prepared using the compounds of Examples 1, 1(a) and 1(b) in the same manner as described in Examples 3 to 6.

We claim:

1. A prostaglandin E₁ analogue of the formula:

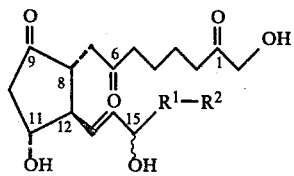

[wherein R¹ represents a direct bond or a straight- or branched-chain alkylene group containing from 1 to 5 carbon atoms(s), and R² represents a hydrogen atom, a straight- or branched-chain alkyl group containing from 1 to 8 carbon atom(s), a cycloalkyl group containing from 4 to 7 carbon atoms in the ring and unsubstituted or substituted by at least one straight- or branched-chain alkyl group containing from 1 to 8 carbon atom(s) or a phenyl or phenoxy group unsubstituted or substituted by at least one halogen atom, trifluoromethyl group or straight- or branched-chain alkyl group containing from 1 to 4 carbon atom(s), with the proviso that, when R¹ represents a direct bond, R² does not represent a phenoxy group] or a cyclodextrin clathrate thereof.

2. A prostaglandin analogue according to claim 1 wherein R¹ represents a direct bond or a methylene group and R² represents an n-pentyl, n-hexyl or n-heptyl group unsubstituted or substituted by one or more methyl groups or represents a cyclopentyl or cyclohexyl group, unsubstituted or substituted by an alkyl group containing from 1 to 8 carbon atoms, or a phenoxy group unsubstituted or substituted by a chlorine atom.

3. A prostaglandin analogue according to claim 1 wherein (i) R¹ represents a direct bond, and R² represents a cycloalkyl group containing from 4 to 7 carbon atoms in the ring unsubstituted or substituted by a straight- or branched-chain alkyl group containing from 1 to 8 carbon atoms(s), and (ii) wherein the grouping —R¹—R² represents an n-pentyl, n-hexyl or n-heptyl group unsubstituted or substituted by one or more methyl groups.

4. A prostaglandin analogue according to claim 1 wherein the hydroxy group attached to the C-15 carbon atom in general formula (IV) depicted in claim 1 is in α-configuration.

5. A prostaglandin analogue according to claim 1 which is 1-hydroxymethyl-11α,15(S)-dihydroxy-17(S),20-dimethylprost-trans-13-ene-1,6,9-trione.

6. A prostaglandin analogue according to claim 1 which is 1-hydroxymethyl-11α,15(S)-dihydroxy-15-cyclopentyl-16,17,18,19,20-pentanorprost-trans-13-ene-1,6,9-trione.

7. A prostaglandin analogue according to claim 1 which is 1-hydroxymethyl-11α,15(S)-dihydroxy-15-(3-propylcyclopentyl)-16,17,18,19,20-pentanorprost-trans-13-ene-1,6,9-trione.

8. A prostaglandin analogue according to claim 1 which is 1-hydroxymethyl-11α,15(S)-dihydroxy-15-(3-butylcyclopentyl)-16,17,18,19,20-pentanorprost-trans-13-ene-1,6,9-trione.

9. A cyclodextrin clathrate of a prostaglandin analogue as claimed in claim 5, 6, 7 or 8.

10. A pharmaceutical composition useful in the treatment of diseases induced by cyto-damage, or in the treatment of gastric ulceration, which comprises, as active ingredient, an effective amount of at least one prostaglandin analogue of general formula (IV) depicted in claim 1 wherein the various symbols are as defined in claim 1, or cyclodextrin clathrate thereof, together with a pharmaceutical carrier or coating.

* * * * *